United States Patent [19]

Smith

[11] Patent Number: 4,842,601
[45] Date of Patent: Jun. 27, 1989

[54] ACCOMMODATING INTRAOCULAR LENS AND METHOD OF IMPLANTING AND USING SAME

[76] Inventor: S. Gregory Smith, Cloud Farm, Nine Gates Rd., Yorklyn, Del. 19736

[21] Appl. No.: 50,782

[22] Filed: May 18, 1987

[51] Int. Cl.$^4$ .............................................. A61F 2/16
[52] U.S. Cl. ......................................................... 623/6
[58] Field of Search .......................................... 623/6

[56] References Cited

U.S. PATENT DOCUMENTS

| | | | |
|---|---|---|---|
| 4,253,199 | 3/1981 | Banko | 623/6 |
| 4,373,218 | 2/1983 | Schachar | 623/6 |
| 4,562,600 | 1/1986 | Ginsberg et al. | 623/6 |
| 4,585,457 | 4/1986 | Kalb | 623/6 |
| 4,608,049 | 8/1986 | Kelman | 623/6 |
| 4,619,662 | 10/1986 | Juergens, Jr. | 623/6 |
| 4,661,108 | 4/1987 | Grendahl et al. | 623/6 |
| 4,693,716 | 9/1987 | MacKool | 623/6 |
| 4,710,194 | 12/1987 | Kelman | 623/6 |
| 4,737,322 | 4/1988 | Bruns et al. | 623/6 X |

*Primary Examiner*—Ronald L. Frinks
*Attorney, Agent, or Firm*—Peterson, Wicks, Nemer & Kamrath

[57] ABSTRACT

A deformable intraocular lens includes first and second plastic lens members connected to each other adjacent their peripheral edges so as to provide a cavity therebetween. The connection is realized by means of a U-shaped flange on the first member forming an inwardly facing groove that receives therein an outwardly extending flange on the second member. The U-shaped flange has a pair of angularly spaced entrance slots through which the flange on the second member is inserted. A biasing arrangement is disclosed for urging the lens members into an expanded relation. The amount of biasing force is correlated with the capability of the natural lens capsule of a human eye so that the intraocular lens can be substituted for the cataractous natural lens. Thereafter, the muscular action exerted on the natural capsule will cause my intraocular lens to flatten and thereby change the focusing thereof. Either or both of the lens members may vary in thickness to provide an additional amount of refractive correction.

30 Claims, 5 Drawing Sheets

ACCOMMODATING INTRAOCULAR LENS AND METHOD OF IMPLANTING AND USING SAME

BACKGROUND OF THE INVENTION

1. Field of the Invention

This invention relates generally to intraocular lenses, and pertains more particularly to a focusable intraocular lens which is substituted for a defective (usually cataractous) natural lens of a human eye.

2. Description of the Prior Art

Various nonfocusable or nonaccommodating intraocular lenses have been devised and rather extensively utilized. One such lens is disclosed in U.S. Pat. No. 4,466,705, issued on Aug. 21, 1984 to Paul E. Michelson for "FLUID LENS." In this instance, a semipermeable sheath having anterior and posterior portions, which portions are joined at their peripheral edges, contain therein a body of liquid. The interior of the sheath is kept full of liquid by osmosis, the liquid in this way determining the refractive power of the lens. The refractive power, however, is not variable.

Lenses of hard plastic have also been devised and used. As an example, reference may be made to U.S. Pat. No. 4,328,595 granted on May 11, 1982 to John H. Sheets for "INTRAOCULAR LENS." This patent depicts a typical plano-convex hard plastic lens that is held in place by means of spring loops. It is of the non-accommodating or non-focusing type in that the lens is simply implanted after the natural lens capsule has been removed.

A more complex and sophisticated system is described in U.S. Pat. No. 4,373,218 issued on Feb. 15, 1983 to Ronald A. Schachar for "VARIABLE POWER INTRAOCULAR LENS AND METHOD OF IMPLANTING INTO THE POSTERIOR CHAMBER" in which the optical characteristics are determined by varying the amount of fluid contained in an expansible sac in one instance, or by means of a controlled voltage in another instance where the contents of the sac constitute a liquid crystal material.

In still another patent, this being U.S. Pat. No. 4,253,199 granted on Mar. 3, 1981 to Anton Banko for "SURGICAL METHOD AND APPARATUS FOR IMPLANTS FOR THE EYE," the natural eye lens is removed along with the anterior portion of the natural capsule. In this situation, the implant capsule is comprised of peripherally sealed pieces or walls that are connected to the ciliary body by means of sutures. The ciliary body provides the muscular action in order to produce different degrees of accommodation.

None of the above patented arrangements, or others known to me, envisage the retention of the biologically provided capsule or bag belonging to a human eye, and replacing the natural lens that has become defective for some reason with a readily deformable lens in which the anterior and posterior walls thereof are normally biased outwardly in a bulging relation with respect to each other, but which can be flattened or caused to move closer together by the natural capsule that has been left within the eye and also the muscle-acting zonules that nature has provided and which also are left within the eye so that they can exert a tensional pull on the natural capsule with the consequence that an artificial lens can be flattened so as to change the refractive index thereof.

SUMMARY OF THE INVENTION

Accordingly, a general object of my invention is to provide an artificial lens that will simulate the action of a natural lens. In this regard, an aim is to retain the biologically provided capsular bag and insert therein my accommodating intraocular lens so that the muscular action normally provided by the zonules connected to the natural capsule will exert a tensional pull outwardly so that the walls of the capsular bag will contract and thus flatten the walls of my substitute intraocular lens.

A more specific object of my invention is to provide an accommodating intraocular lens that will normally be biased into a more spherical or bulging shape with portions of the anterior and posterior walls spaced farther apart along the optical axis of the lens so as to correct for near vision and to enable the lens to be flattened more for distance vision.

Associated with the preceding object is the advantage that my invention permits the choice and employment of several different types of biasing mechanisms, thereby enabling the biasing action to be more closely correlated with the gentle muscular forces that are applied to the natural lens capsule. For instance, the biasing action may be provided by the lens members themselves, if the proper material and thickness are selected, or by supplemental spring-like devices.

Another object is to provide a two-piece intraocular lens, in which the two lens members can be readily assembled without having to resort to heat or sonic sealing procedures. More specifically, my invention lends itself to being easily assembled within the natural lens capsule after removal of the person's biological lens.

Still another object is to incorporate some of the refraction power of the assembled lens in either or both of the lens members by reason of the radii of curvature imparted to the outer and inner surfaces thereof.

A further object of the invention is to provide an accommodating intraocular lens that can be readily implanted. In this regard, my invention allows the surgeon to utilize known incising techniques in order to provide access to the natural lens contained within the biologically provided capsular bag, then permitting the removal of the natural lens, and then inserting or implanting my accommodating intraocular lens, preferably in two stages, within the cavity of the capsule that has originally contained the natural lens therein. If desired, the anterior portion of the natural capsule can then be sutured so as to retain permanently a lens structured in accordance with my invention.

Yet another object is to provide an accommodating or focusable intraocular lens that is not only relatively inexpensive to manufacture or fabricate, but can be relatively easily implanted. In this way, the cost of the overall operation is kept to a minimum.

Briefly, my invention contemplates the provision of a two-piece intraocular lens having focusing or accommodating capabilities that is comprised of a pair of flexible plastic walls or lens members that are configured so as to be readily secured together adjacent their edges so that the lens members can be flexed to change the distance therebetween. In this way, the distance between the lens members, as measured along the optical axis of the lens, can be either increased or decreased to permit the eye to focus on either nearby or distant objects. It is planned that the flexible walls or lens members be normally biased into a more spherical or bulging relationship so that the eye is normally adjusted or focused on closer items but capable of being flattened. The overall refractive power of my intraocular lens can also be modified by employing individual flexible lens members that are themselves refractive.

When my two-piece intraocular lens is implanted in the biologically provided capsule, preferably in two stages or steps, the capsule thereafter functions in the same manner that nature intended. More specifically, the zonules, which remain connected to the natural capsule, continue to exert a muscular force in a direction to flatten the intraocular lens so that the refractive index is changed to enable distant objects to be viewed by reason of the contractive capability of the natural capsule against the anterior and posterior walls of my substituted lens. Several types of resilient means are made use of in achieving the biasing action that causes the lens to assume a more spherical or bulging shape, yet permitting the walls of the lens to flatten so as to accommodate or focus the eye on distant objects. Thus, the zonules, which remain in place, exert a muscular control so as to overcome the biasing action that normally causes the intraocular lens to assume a more spherical shape.

BRIEF DESCRIPTION OF THE DRAWINGS

FIG. 7 represents the more advanced view of the second lens member of my intraocular lens as it is being implanted, the implanting stage corresponding to the phantom line relationship thereof appearing in FIG. 4;

FIG. 8 is a perspective view similar to FIG. 3 but showing a segmental portion of the second lens member partially inserted into the first lens member via the two entrance slots, one of which entrance slots is detailed in FIGS. 5 and 6;

DESCRIPTION OF THE PREFERRED EMBODIMENTS

Figure 1:
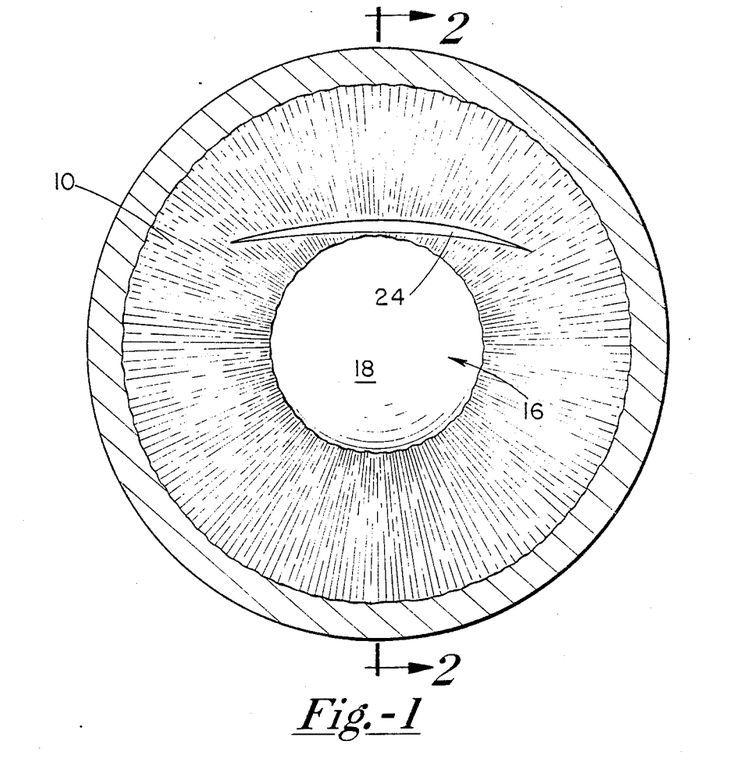
FIG. 1 is a top plan view of the anterior lens capsule and surrounding iris of a human eye in which my accommodating intraocular lens is about to be implanted the view being taken generally in the direction of line 1—1 of FIG. 2 at a level beneath the cornea and the patient whose eye is being operated on being considered to be in a prone position looking up.
Figure 2:
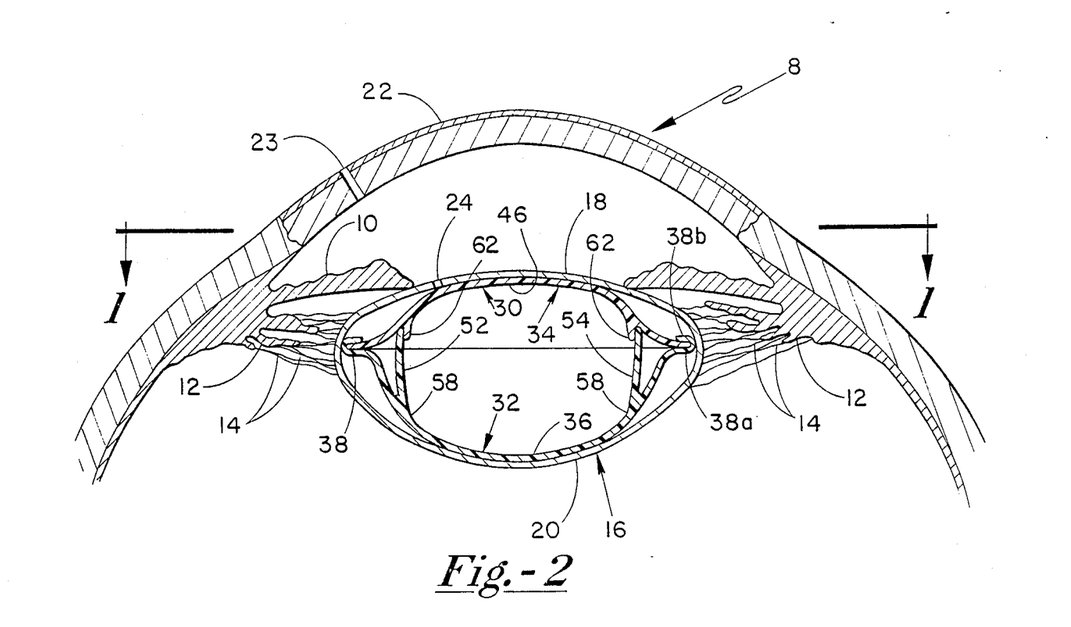
FIG. 2 is a relatively diagrammatic sectional view taken in the general direction of line 2—2 of FIG. 1, but with the cornea present, the view depicting my intraocular lens in an assembled condition after its component parts have been sequentially implanted in the natural capsule of the eye.

Referring now to FIGS. 1 and 2, a somewhat diagrammatic representation of an eye has been indicated generally by the reference numeral 8. It is to be noted that the eye 8 includes only certain basic parts believed sufficient to illustrate the benefits to be derived from a practicing of my invention. In this regard, there is an iris 10, a ciliary body 12, zonules 14 extending from the ciliary body 12 to the biologically existing capsule or capsular bag 16 having an anterior portion or wall 18, frequently termed an anterior capsule, and a posterior portion or wall 20, frequently termed a posterior capsule. As is well known, the zonules 14 exert a pulling or tensional force on the capsular bag 16, causing the capsular bag 16 to assume a more flattened configuration than its usual more spherical shape. Although not shown in FIG. 1, FIG. 2 includes the cornea that has been labeled 22.

An incision 23 of appropriate length is first made in the cornea 22 and then a second incision 24 of about nine or ten millimeters in length is then made by the surgeon in the capsule 16 for the purpose of first removing the natural lens (not illustrated) and thereafter substituting for the natural lens my accommodating intraocular lens 30 which will be described hereinafter.

At this time, attention is directed to U.S. Pat. No. 3,996,935, issued on Dec. 14, 1976 to Anton Banko for "SURGICAL-TYPE METHOD FOR REMOVING MATERIAL" in which the patentee describes an extra capsular procedure in which the natural lens is removed without destroying or taking out the natural capsule or bag 16. As described in U.S. Pat. No. 3,996,935, a 20 millimeter incision is necessary in the outer wall of the eye in order to reach the anterior portion of the natural capsule. Relating this to the present situation, it can be pointed out that the incision 24 need not be as long as 20 millimeters, instead being on the order of only nine or ten millimeters, as already stated. Furthermore, it is planned that the incision 23 be made in the cornea 22 in contradistinction to the location selected and depicted in U.S. Pat. No. 3,996,935.

Having prefaced a description of my invention with the foregoing, attention is directed to FIG. 2 in which the natural lens has been replaced with the accommodating intraocular lens 30 exemplifying my invention. Although the construction of my lens 30 has not yet been presented, it will facilitate an understanding of the invention to recognize that the lens 30 is readily deformable by the natural capsule or capsular bag 16 so as to change the index of refraction thereof, the zonules 14, when exerting a tensional pull on the capsular bag 16, causing the lens 30 to become flattened to a greater degree. Normally, though, the lens 30 is biased into its more spherical or bulging shape, as will be better understood hereinafter.

Figures 7, 8, 11:
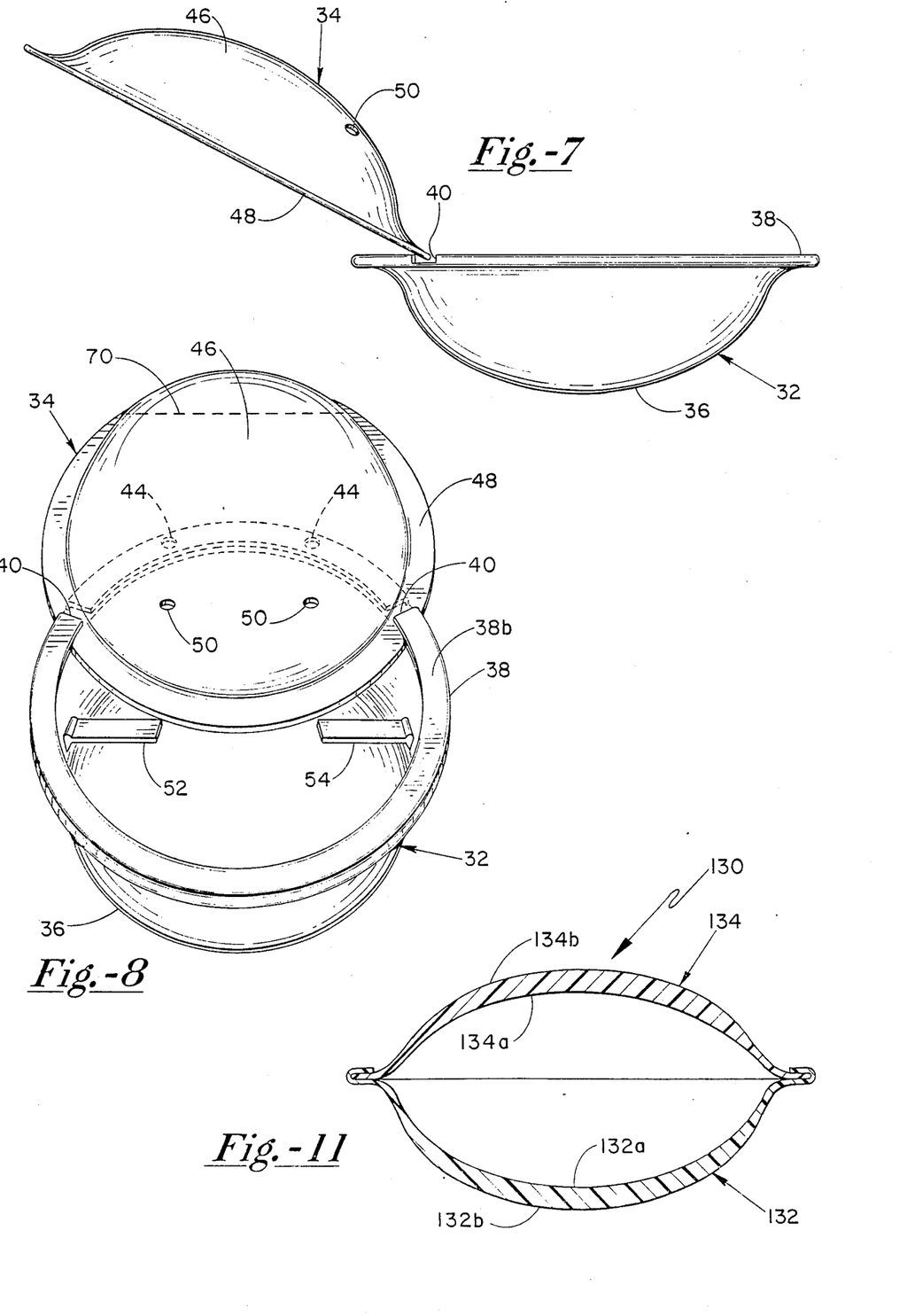

Referring now in detail to the construction of the intraocular lens 30, it will be noted that the lens 30 comprises two flexible membrane-like lens members 32 and 34, the member 32 being a posterior member and the member 34 being an anterior member when implanted. For the sake of simplicity, the thickness of the lens members 32 and 34 (with the exception of those appearing in FIG. 11) are of uniform thickness. In FIG. 11, the thickness of the lens members is varied so as to impart a predetermined amount of fixed refraction to that particular embodiment of my lens.

Obviously, the members 32 and 34 must be transparent, and basically they can be selected from a family of plastic polymers. Certain materials have in the past been used in the making of soft contact lenses and such materials are suitable as far as my intraocular lens 30 is concerned. In this regard, silicone, fluorocarbons, or HEMA and PMMA which is polymethylmethacrylate or suitable materials. Whereas polymethylmethacrylate is normally quite hard, it can be blended with silicone in order to impart thereto an acceptable degree of resiliency and softness. Although the thickness of the lens members 32 and 34 will depend to a certain extent upon the particular material selected, it can be stated that as a general matter the thickness will be on the order of from 0.2 to 0.3 millimeter. As the description progresses, it will become apparent that there should be sufficient resiliency imparted to the members 32 and 34 so as to cause them to bulge or expand along the optical axis of the lens 30. Several biasing mechanisms or devices will also be described later.

Inasmuch as it is believed that an understanding of my invention will be made easier by having assumed that the lens 30 has been already implanted and is fully assembled within the natural capsular bag 16, reserving the implanting procedure to later on, the manner in which the two lens members 32 and 34 are held together will now be described. In this regard, the lens members 32 and 34 differ considerably from each other. As will hereinafter be explained, the posterior lens member 32 is the one that is first inserted into the natural capsule or bag 16. THerefore, it will be well to describe the construction of the posterior lens member 32 at this point. It will also help, it is believed, to refer to the lens member 32 in the relation it assumes when the patient is in a prone position, such as during the implanting operation. With this in mind, it will be seen that the lens member 32 has a downwardly bulging central portion 36, the bottom surface of which is convex whereas the upper surface of which is concave. The portion 36 need not be circular, but it is somewhat simpler to consider it as being circular and possessing an eight millimeter diameter; the portion 36 provides what can be termed the optical zone.

Figure 6:
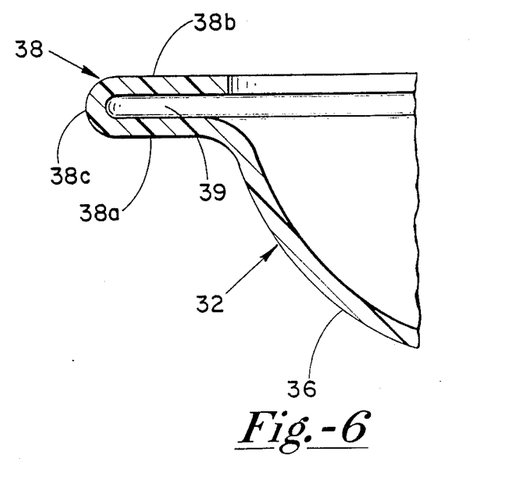
FIG. 6 is an enlarged sectional detail taken in the direction of line 6—6 of FIG. 3 to further illustrate the configuration of the entrance slot at that side.

Extending peripherally or marginally around the optical zone or central portion 36 is a U-shaped flange 38 having a width of two millimeters. More specifically the flange 38 is composed of what might be considered to be a leg portion 38a which forms a circular ring extending peripherally around the central portion 36. The U-shaped configuration of the flange 38 is perhaps best understood from FIG. 6. Thus, there is an additional leg 38b that constitutes another ring portion that is spaced above the leg portion 38a, the portions 38a and 38b being integrally connected by reason of a bight portion 38c to form a groove labeled 39.

Figure 3:
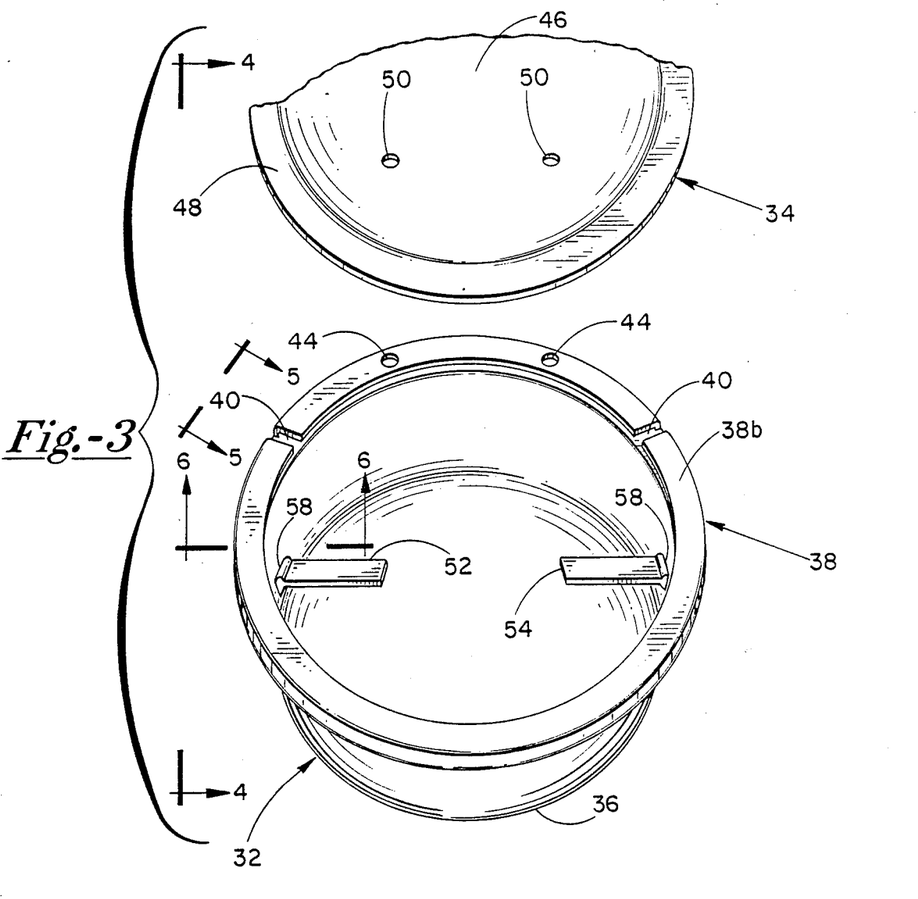
FIG. 3 is an angled perspective view taken generally in the direction of line 3—3 of FIG. 2 but viewed downwardly at about 45° from the bottom of the sheet, the view illustrating one lens member in the horizontal position (by virtue of the patient being in a prone position and looking up) in which it would reside in the natural capsule (although the natural capsule is not pictured) and the second lens member in the process of being moved angularly downwardly at about 45° from the top of the sheet by the surgeon (also not shown) toward the first lens member.
Figure 4:
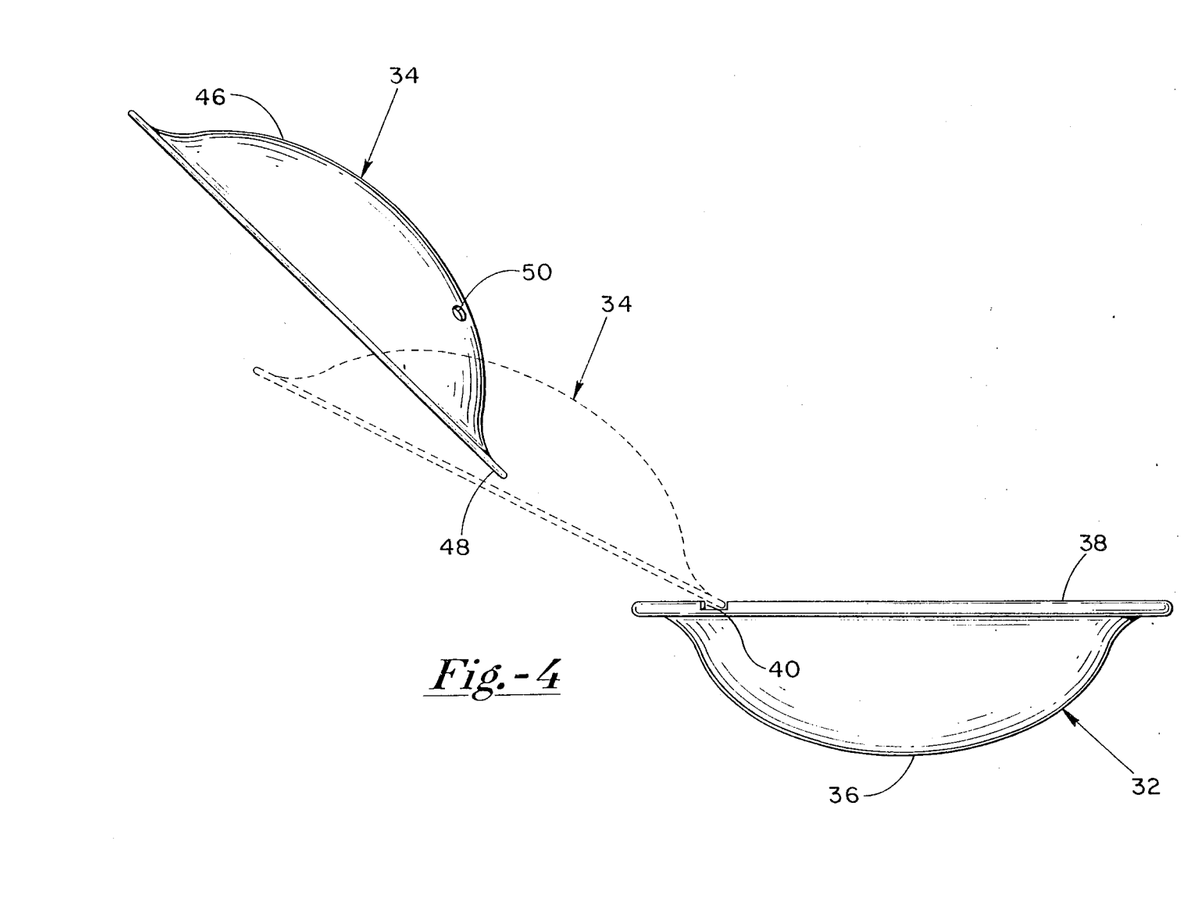
FIG. 4 is a side elevational view taken in the direction of line 4—4 of FIG. 3, the view depicting the second lens member of FIG. 3 at the 45° angle in which it is moved by the surgeon and the phantom position thereof denoting a more advanced position thereof.
Figure 5:
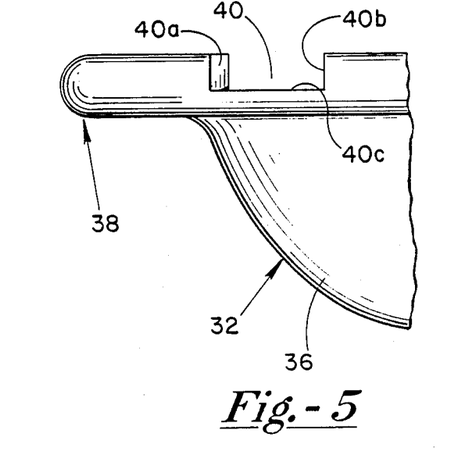
FIG. 5 is a fragmentarily depicted, enlarged elevational detail taken in the direction of line 5—5 of FIG. 3 for the purpose of better showing one of the two entrance slots utilized in the insertion of the second lens member into engagement with the first lens member that has already been implanted in the natural capsule of the eye.

In order for the anterior lens member 34 to be mated with (that is, connected to) the posterior lens member 32, a pair of entrance slots 40 are formed in the U-shaped flange 38. As perhaps best understood from FIG. 3, these slots 40 are located at the 2 o'clock and 10 o'clock positions. In some situations, the slots 40 can be closer to the 12 o'clock position. It depends upon the deformability of the particular materials that are selected for the two lens members 32 and 34. From FIG. 5, it will be discussed that the slot 40 extends a little more than half way down as far as the bight portion 38c is concerned. As can be appreciated from FIG. 5, the slot 40 appearing in this view has vertical edges 40a and 40b and a horizontal edge 40c. However, the edges 40a and 40b need not be vertical, for they can slope in order to facilitate the insertion or connective engagement of the anterior member 34 with the posterior member 32. It will be noted, though, that a pair of holes 44 are formed in the leg portion 38b of the U-shaped flange 38. These holes 44 aid in the insertion of the posterior lens member 32 into the capsule 16. The holes 44 additionally serve as a positioning means for properly orienting the lens member 32 within the capsule 16.

Turning now to a description of the construction of the anterior lens member 34, it will be observed that it has a central bulging portion 46 having a diameter corresponding to that of the central portion 36, that is, eight millimeters. Integrally attached to the central portion 46, which functions as the optical zone for the anterior lens member 34, and extending radially outwardly from the portion 46, is a planar flange 48 having a width of 1.5 millimeters so as to be receivable in the groove 39. As with the posterior lens member 32, the anterior lens member 34 is also provided with positioning holes, these positioning holes being indicated by the reference numeral 50.

As believed evident, the lens members 32 and 34, more specifically, their central portions 36 and 46, respectively, bulge outwardly with respect to each other when connected along their edges and are yieldably biased in a direction to increase the distance therebetween in order to have them normally assume a more spherical configuration. While it is possible to select materials and mold them so that they will possess an inherent degree of outward biasing which would allow repeated bi-directional movement of the central portions 36 and 46 relative to each other, it is planned that auxiliary means be adopted to achieve the proper amount of biasing action. The correct amount of biasing action is very important inasmuch as the lens members 32 and 34 must be susceptible to being flattened by the gentle squeezing action provided by the natural capsular bag 16 that is retained within the eye 10. In other words, the amount of biasing force must be correlated with the capability of the natural capsule 16 to contract its portions 18 and 20. Stated somewhat differently, the portions 36 and 46 must be sufficiently deformable in order to allow them to assume a less spherical relationship with each other. The contractile force is provided exclusively from the pressing of the anterior portion 18 against the portion 46 and the posterior portion 20 against the portion 36. As is generally recognized, the squeezing action provided by the natural capsular bag 16 is derived by way of the zonules 14 which are muscularly controlled by the ciliary body 12.

Figure 9:
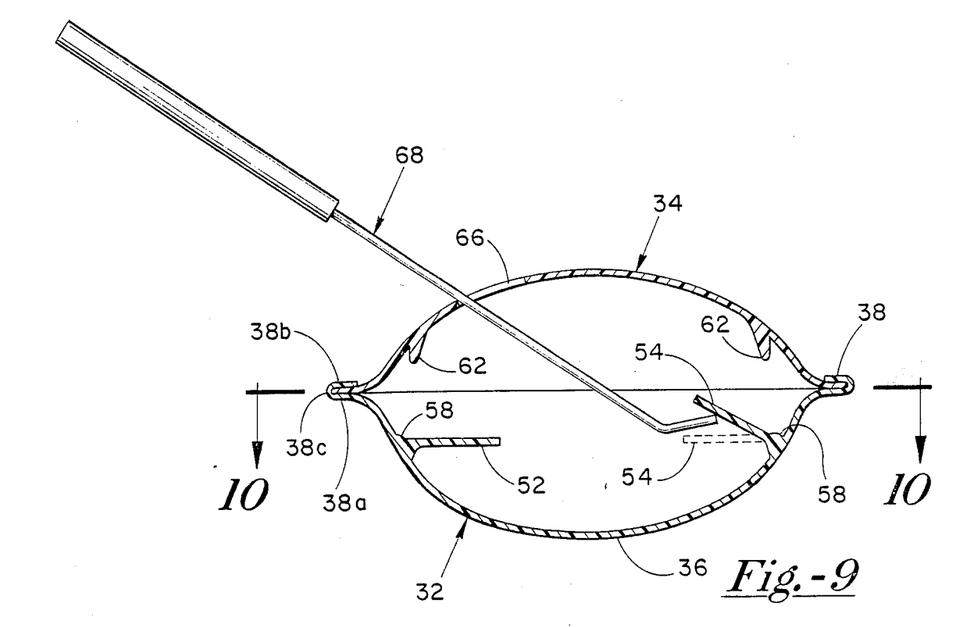
FIG. 9 is a sectional view of my intraocular lens as it appears in FIG. 2, but illustrating how the bowed resilient strips of FIG. 2, which constitute a biasing mechanism, are swung upwardly from their unflexed condition into their bowed condition.
Figure 10:
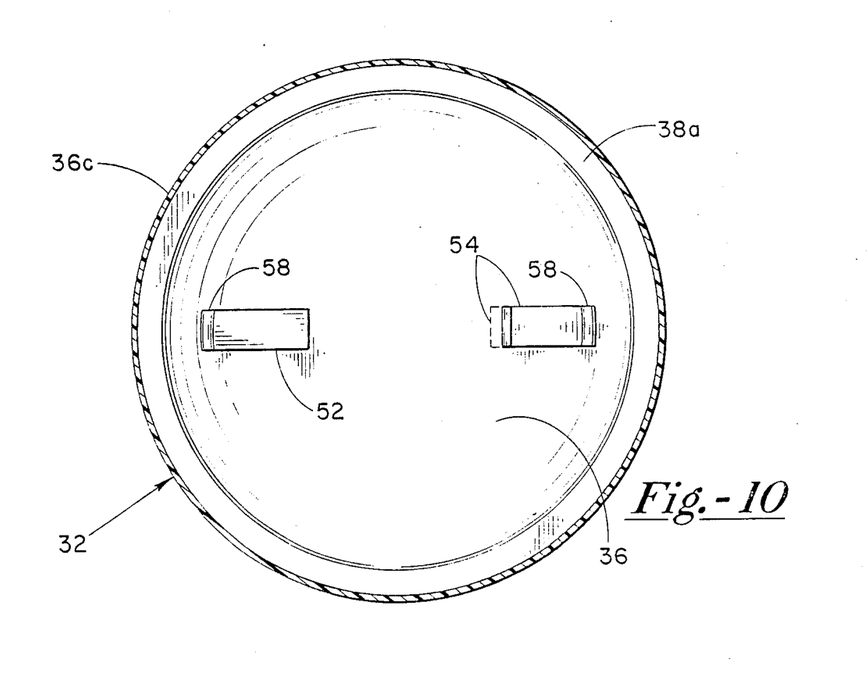
FIG. 10 is a sectional view taken in the direction of line 10—10 of FIG. 9 for the purpose of depicting to better advantage the unflexed shape of the resilient strips, and FIG. 11 constitutes a view generally resembling FIG. 2, but illustrating my intraocular lens in which the two lens members are light refractive by reason of the different curvature imparted to their inner and outer surfaces.

Although the biasing action may be supplied by the lens members 32 and 34, such as by thickening portions thereof or by using a material that will possess the requisite degree of resiliency, it is planned that a biasing mechanism or device be employed. Therefore, one such mechanism is illustrated in FIGS. 2, 9 and 10, although appearing in phantom outline in FIG. 9. The mechanism is in the form of a pair of resilient strips 52 and 54, one strip 52 being nearer one side of the lens 30 and the other strip 54 being nearer the opposite side thereof. These strips 52, 54 are preferably of PMMA, the same material as the lens members 32, 34, but not as flexible or pliable as the members 32, 34 in that the strips 52, 54 should to same extent resist deformation, possessing, however, a considerable amount of "memory." Inasmuch as the function of these strips 52 and 54 is to increase the stiffness of the lens members 32 and 34, they need only be anchored to the inner or upper surface of the posterior lens member 32 along one end thereof, as indicated by the reference numeral 58 in FIGS. 2, 9 and 10. Inasmuch as the lens member 32 and the strips 52, 54 can both be of the same material (PMMA) but possessing different degrees of pliability, the securement, as indicated by the reference numeral 58 can be by means of heat sealing (although a suitable adhesive can also be employed). The securing of the one end in each instance is done before the lens member 32 is implanted.

The other end of each resilient strip 52, 54 is anchored to the upper lens member 34 through the agency of a rib 62 that is integral with the underside or lower surface of the lens member 34. The technique for effecting the engagement is pictorially presented in FIGS. 9 and 10, but is better left for discussion hereinafter.

The central portions 36 and 46 of the lens members 32, 34 normally assume a more spherical shape than they otherwise would. It is essential, however, that the outward biasing action supplied by the strips 52, 54 not be so great as to resist the needed contraction or flattening of the central or bulging portions 36 and 46 which action is produced by the action of the capsular bag 16 when it is flattened by the muscular action derived from the various zonules 14. It will be recalled that the zonules 14 and the ciliary body 12 are retained, along with the natural lens capsule 16, in the eye 10.

As already explained, the hereinbefore identified Banko patent describes a general procedure for initially removing the natural lens. It may be helpful to explain in greater detail the procedure actually utilized when practicing my invention. Therefore, after the surgeon has first made the access incision 23 (FIG. 2) in the cornea 22, he then performs what is termed an anterior capsulotomy in which a sharp needle on a hypodermic syringe is made use of, the tip of the needle being bent down so as to make the incision 24 in a direction from the 2 o'clock to the 10 o'clock position of the eye 10, as viewed in FIG. 1. After this, the surgeon, using the same needle, slides it underneath the natural capsule 16 and injects fluid which loosens the cortex of the nucleus of the natural lens so that it no longer adheres to the natural capsule 16.

It is believed evident that the optical power of the intraocular lens 30 can be varied by adjusting the spacing between the members 32 and 34. It might be stated at this point that the natural lens which is completely removed when practicing my invention, is usually considered to involve anterior and posterior poles. A line connecting the poles constitutes the axis of the natural lens whereas the marginal circumference would be termed the equator. Thus, my invention enables the line connecting the poles, that is along the axis, of the lens 30, to be shortened in order to permit the viewing of far away objects. Stated somewhat differently, whereas the lens members 32, 34 are normally expanded with a concomitantly greater amount of refraction, as they will be when viewing nearby objects, a lesser amount of refraction is realized when the lens members 32, 34 are closer together and possess a more flattened configuration.

However, the refractive power of my intraocular lens does not have to reside solely in the variable spacing between the members 32 and 34. This is why FIG. 11 has been presented. It will be well to assign the reference numeral 130 to the intraocular lens depicted in this figure with the lens members 132 and 134 having the capability of providing an initial refractive power. Consequently, it will be noted from FIG. 11 that the posterior lens member 132 has an upper or inner concave surface 132a that has a lesser radius of curvature than its lower or outer surface 132b. By the same token, the anterior lens member 134 has a lower or inner surface 134a having a lesser radius of curvature than its upper or outer surface 134b.

The intraocular lens 130, however, will still have its refractive power varied in the same manner as that derivable from the lens 30. In other words, the initial refraction obtained from the different thickness of the members 132 and 134 serves as a basis from which additional refractive power is derived. Thus, whereas the thicknesses of the members 132 and 134 differ throughout their surface areas 132a, 132b and 134a, 134b, the surfaces 132a and 134a will be acted upon by the natural lens capsule 22 so as to flatten these members 132, 134 to a greater degree than that pictured in FIG. 11. In other words, there can be provided a basic optical power in the posterior lens member 132 and a similar optical power in the anterior lens member 134. Of course, it will be recognized that the radius of curvature of the inner surface 132a of the posterior lens member 132 can be different from that of the surface 134a of the anterior member 134, and that the radii of curvature of the surfaces 132b and 134b can likewise differ from each other. In this way, the member 132 can constitute one lens having one fixed optical power, and the other member 134 can constitute a lens with a different optical power.

The point to be recognized is that the optical power can be literally ground into the lens members 132, 134 so as to provide an initial accommodation or focusing power for the particular individual to be fitted with my intraocular lens 130. Of course, the accommodation or focusing power, as already explained, is still preserved in that the distance along the optical axis, that is the distance between the members 132, 134, will still provide the person with the capability of viewing close-up objects, as is possible when the members 132, 134 are bulging or spaced farther apart along the axis of the lens 130, that is more expanded, in contradistinction to when they are gently squeezed or urged toward each other by the capsular bag 16 so that they then assume a flatter condition which, in the latter case, focuses the lens 130 for viewing more distant objects.

The diameter of my lens 30 or 130 is dictated by the physical dimensions of the portions of the eye 10. Normally, the diameter will be approximately twelve millimeters (where the portion 36 has a diameter of eight millimeters and the flange has a width of two millimeters of each side of the lens member 32). The degree of change in the anterior/posterior dimensions will be from 1 to 2 millimeters, this change being produced by the pull of the zonules 14 when exerting their muscular control over my lens 30 to 130. It must be borne in mind that the capsular bag 16, which is of biological origin, is retained within the eye 10 and made use of when practicing my invention.

Once having performed the above, the material within the natural lens is fairly loose. It is then that an irrigating vectis, being a loop-like device, is slid beneath the hard part of the natural lens so that the natural lens is completely free and can be lifted up and out of the natural capsule 16 of the eye 10, doing so through the incisions 23 and 24. There may at times be some residual cortex, which is a soft part of the cataract (assuming that the implant is prompted by a cataractus condition), and at this point another special cannula is made use of which irrigates on one side and aspirates on the other side, enabling the soft residual material to be stripped from the natural capsule throughout its entire area, that is throughout 360 degrees, thereby leaving the natural capsule with a clear inner surface.

It is at this stage that the eye 8 is ready for my lens 30 to be implanted therein. The lens members 32 and 34, as is evident, constitute a two-piece lens 30 when assembled. First, the posterior lens member 32 is inserted into the natural lens capsule 16, which has been completely cleaned as described above, by grasping the U-shaped flange 38 of the lens member 32 in the region of the positioning holes 44. Actually, the forceps can be designed to have its angled jaws or pincer ends receivable in the holes 44. In any event, the forceps are employed to literally push the posterior lens member 32 through the incisions 23 and 24 so that it then resides within the cavity of the natural lens capsule 16. Owing to the deformability of the lens member 32, it can be folded to whatever extent is needed to enable it to pass through the incision 24 (and of course the incision 23 in the cornea 22) that has been initially provided for the extraction of the natural lens.

Once the posterior lens member 32 has been inserted or implanted, the next step is to insert or implant the other lens member 34. This is done by inserting the anterior lens member 34 through the same incision 24. In doing so, the surgeon must be careful to first position or orient the posterior lens member 32 so that is positioning holes 44 reside to either side of the 12 o'clock position. Utilizing the positioning holes 50 and the same or similar forceps, the anterior lens member 34 is pressed inwardly through the incision 24. It is at this time that the surgeon must be careful to guide the flange 48 through the slots 40, formed in the U-shaped flange of the now in place posterior lens member 32. The surgeon may very well wish to use two forceps, holding the posterior lens member 32 with one while guiding the other lens member 34 through the slots 40. It is believed that this sequential action is aptly understood from FIGS. 3, 4, 7 and 8. The surgeon, once the flange 48 has been inserted into the slots 40 continues to advance the anterior lens member 34 into the groove 39 of the U-shaped flange 38, doing so in a gentle manner.

Once the anterior lens member 34 has been advanced so that its flange 48 is fully received in the groove 39 formed in the U-shaped flange 38, there remains a segmental portion of the anterior lens member 34 that must literally be tucked into that portion of the groove 39 extending between the slots 40. While it is assumed that the anterior lens member 34 will have a circular shape, somewhat less in diameter than the outer diameter of the lens member 32 (by about 0.5 millimeter) it can, depending upon the stiffness of the lens member 34, turn out that a segmental portion of the lens member 34 extending somewhat to either side of the 12 o'clock position be cut off or severed so that the flange 48, for the most part, will reside throughout its periphery within the groove 39. The surgeon will know from previous experiences as to whether it is necessary to remove a segmental portion of the anterior lens member 34. When a segmental portion is to be removed, it will be generally along the dashed line labeled 70 in FIG. 8. This might very well leave a chord-like opening. However, even though such an opening would permit some of the eye fluid to enter into the cavity of the assembled lens 30 occupied almost completely by my lens 30 (or 130), it does not interfere with the focusing capability of lens 30. As a matter of fact, some fluid might very well enter through the holes 44 and 50.

As already indicated, it is contemplated that the biasing mechanism in the form of the resilient strips 52, 54 be attached to the posterior lens member 32 before the implanting step. Once the two lens members 32 and 34 have been completely engaged and assembled with each other, then the members 52, 54 can be literally uprighted or moved through 90°. To do this, an incision 66 (or two equally-spaced incisions) is made. This incision 66 can actually be made prior to the implanting of the lens member 34 (or 134), but it simplifies the drawings to show the incision 66 only in FIG. 9. An appropriately angled implement 68 is then inserted through the incision 66 by the surgeon and its free end used to tilt the resilient strip 54 from its horizontal or dotted position of FIG. 9 through the 45° inclination or solid line position thereof in FIG. 9 into the vertical position depicted in FIG. 2. The inserted or free end of the implement 68 simply presses against the strip 54 to whatever extent is necessary to cause the strip 54 to bow or curve sufficiently to allow its free end to literally snap into place behind the rib 62, as shown in FIG. 2. The strip 52 is manipulated in the same manner, preferably by using the same incision 66. However, a second incision 66 can be made, such second incision 66 then being adjacent the right-hand rib 62, as viewed in FIG. 9.

Whether it be the lens 30 or the lens 130, the capability of focusing is provided so that the user can see objects to him or her when less compressive action is supplied by the natural capsule 16. When objects farther away are to be viewed, then the lens 30 or 130, as the case may be, becomes considerably flatter, becoming so in virtually the same manner as is done when relying on an undamaged natural lens.

I claim:

1. An accommodating intraocular lens comprising first and second flexible membrane-like lens members adapted to be inserted into a natural human lens capsule, said members having mutually interengaging means for connecting each other adjacent their edges after insertion into a natural human lens capsule, said lens members being yieldably biased in a direction to increase the distance therebetween and to thus produce a normal bulging thereof so as to allow a repeated bi-directional movement of central portions of said members relative to each other when subjected to the muscular or contractile action of a natural human capsule, the amount of yieldable biasing force being correlated with the capability of the natural capsule to contract and overcome the amount of biasing force to thereby reduce the amount of said normal bulging.

2. An accommodating intraocular lens in accordance with claim 1 including resilient means for biasing said lens members in said direction to increase the distance therebetween and to produce said normal bulging, said resilient means being sufficiently yieldable to permit movement of said central portions of said lens members in a reverse direction when subjected to said muscular or contractile action to thereby reduce the amount of said normal bulging.

3. An accommodating intraocular lens in according with claim 2 in which said biasing means includes at least one resilient member disposed between said members and anchored to the inner surface of at least one of said lens members.

4. An accommodating intraocular lens in accordance with claim 3 in which said one lens member is a posterior member.

5. An accommodating intraocular lens in accordance with claim 1 in which said lens members are of a polymeric plastic.

6. An accommodating intraocular lens in accordance with claim 5 in which at least one of said lens members has a positioning hole formed therein adjacent an edge thereof to facilitate positioning of said one lens member with the other of said lens members.

7. An accommodating intraocular lens in accordance with claim 1 in which at least one of said lens members integrally varies in thickness to change the refractive power thereof.

8. An accommodating intraocular lens in accordance with claim 7 in which said one lens member is thicker near the center thereof.

9. An accommodating intraocular lens comprising first and second flexible lens members, said first lens member having a U-shaped peripheral flange forming an inwardly facing groove and said second lens member having a generally planar flange residing in said groove.

10. An accommodating intraocular lens in accordance with claim 9 in which said U-shaped flange has a pair of angularly spaced notches therein via which the flange on said second lens member may be inserted into the groove of said U-shaped flange.

11. An accommodating intraocular lens in accordance with claim 9 in which each of said lens members has a positioning hole formed therein.

12. An accommodating intraocular lens in accordance with claim 9 including means biasing said first and second lens members outwardly.

13. An accommodating intraocular lens in accordance with claim 12 in which said biasing means includes a pair of spaced resilient members acting against the inner surfaces of said lens members.

14. An accommodating intraocular lens comprising first and second flexible lens members connected to each other adjacent their edges, and resilient means normally biasing said lens members in a direction to increase the distance therebetween, said resilient means being in the form of a pair of resilient strips.

15. A method of implanting an intraocular lens in the biological capsule of an eye from which the natural lens has been removed, the method comprising the steps of inserting a posterior flexible lens member into the capsule, inserting an anterior flexible lens member into said capsule so as to engage said posterior lens member, and attaching said lens members to each other along at least portions of their marginal edges, said posterior lens member having a U-shaped marginal flange forming a marginal groove and said anterior member having a flange formed thereon, said attaching step constituting the step of inserting said flange into said groove, said U-shaped flange having a pair of entrance slots via which the flange on said anterior member is inserted.

16. A method of implanting an intraocular lens in the biological capsule of an eye from which the natural lens has been removed, the method comprising the steps of inserting a posterior flexible lens member into the capsule, inserting an anterior flexible lens member into said capsule so as to engage said posterior lens member, each of said lens members being formed with a convexly curved portion so as to form a cavity therebetween, and the step of placing a resilient means within said cavity so as to bias said lens members into a more spherical relationship.

17. A method of implanting an intraocular lens in accordance with claim 16 in which said resilient means is in the form of a pair of resilient strips.

18. A lens member for an intraocular lens comprising a flexible central portion having a U-shaped flange at the margin thereof to form an inwardly facing marginal groove, said flange having a pair of slots therein so that the marginal portion of a second lens member may be inserted into said groove via said slots.

19. A lens member in accordance with claim 18 in which the marginal portion of said second lens member constitutes a planar flange.

20. A method of implanting an intraocular lens in the biological capsule of an eye from which the natural lens has been removed, the method comprising the steps of inserting a posterior flexible membrane-like lens member into the capsule, and then inserting an anterior flexible membrane-like lens member into said capsule so as to engage said posterior lens member.

21. A method of implanting an intraocular lens in accordance with claim 20 including the step of attaching said lens members to each other along at least portions of their marginal edges to thereafter permit bi-directional relative movement of central portions of said lens members.

22. A method of implanting an intraocular lens in accordance with claim 21 in which said posterior member has a marginal groove formed therein and said anterior member has a flange formed thereon, said attaching step constituting the step of inserting said flange into said groove to permit said bi-directional movement of said central portions.

23. A method of implanting an intraocular lens in accordance with claim 22 in which said posterior lens member has a U-shaped marginal flange, said U-shaped flange forming said groove.

24. A method of implanting an intraocular lens comprising the steps of substituting a two-part membrane-like intraocular lens for the natural lens within the complete biological lens capsule of an eye, said steps including the insertion of said parts into said complete capsule after the natural lens has been removed.

25. A method of implanting an intraocular lens in accordance with claim 24 in which each of said parts is of a flexible material.

26. A method of implanting an intraocular lens in accordance with claim 25 in which each of said parts includes a convexly curved portion bulging outwardly to form a cavity between said portions, and placing at least one resilient member within said cavity so as to bias said convexly curved portions outwardly.

27. A method of implanting an intraocular lens in accordance with claim 24 in which the first part that is inserted has a marginal groove formed therein and the second part that is inserted has a marginal flange thereon so that at least a portion of said flange can be received in said groove.

28. A method of implanting an intraocular lens in accordance with claim 27 in which said flange and groove reside in substantially the same plane after said flange is received in said groove.

29. A method of implanting an intraocular lens in accordance with claim 27 in which each of said parts has a hole therein for relatively positioning said parts with respect to each other.

30. A method of using an accommodating intraocular lens comprised of deformable plastic lens members that have been implanted within the natural lens capsule of an eye, said lens members being normally biased away from each other into a more spherical relationship and said natural capsule overcoming the biasing action to change the focusing of the lens member by causing said lens members to be flattened to a greater extent so that the user can view distant objects and when said lens members are biased away from each other into said more spherical relationships the user can view closer objects.

* * * * *